United States Patent [19]
Chory et al.

[11] Patent Number: 6,143,950
[45] Date of Patent: Nov. 7, 2000

[54] PLANT STEROID 5α REDUCTASE, DET2

[75] Inventors: Joanne Chory, Solana Beach; Jianming Li, San Diego, both of Calif.

[73] Assignee: The Salk Institute for Biological Studies, La Jolla, Calif.

[21] Appl. No.: 08/634,475

[22] Filed: Apr. 18, 1996

[51] Int. Cl.[7] .......................... C12N 15/29; C12N 15/82; A01H 4/00; A01H 5/00

[52] U.S. Cl. ..................... 800/298; 800/295; 435/69.1; 435/320.1; 435/419; 536/23.6; 536/24.1

[58] Field of Search ..................... 800/205, 295, 800/298; 435/172.3, 69.1, 320.1, 419; 526/23.6, 24.1

[56] References Cited

PUBLICATIONS

David W. Russell, Green Light for Steroid Hormones, Science, vol. 272:370–371, Apr. 19, 1996.

Brassinosteroids: Chemistry, Bioactivity, and Applications, Eds. H.G. Cutter, T. Yokota, G.Adams, Chapters 24–30, pp. 282–344, ACS Symposium–Series 474, American Chemical Society, Washington, D.C., 1991.

Li, et al., A Role for Brassinosteriods in Light–Dependent Development of Arabidopsis, Science, vol. 272:398–401, Apr. 19, 1996.

Szekeres et al., "Brassinosteroids rescue the deficiency of CYP90, a cytochrome P450, controlling cell alongation and de–etiolation in Arabidopsis", *Cell*, Apr. 19, 1996, vol. 85, No. 2, pp. 171–192.

Li et al., A role for brassinosteroids in light–dependent development of *Arabidopsis, Science,* Apr. 19, 1996, vol. 272, No. 5260, pp. 398–401.

Russel et al., "Green Light for Steroid hormones," *Science,* Apr. 19, 1996, vol. 272, No. 5260, pp. 370–371.

*Primary Examiner*—Douglas W. Robinson
*Assistant Examiner*—Thomas Haas
*Attorney, Agent, or Firm*—Fish & Richardson P.C.

[57] ABSTRACT

A novel plant steroid 5α reductase, DET2, is provided, as well as polynucleotides encoding DET2. DET2 is useful in promoting increased plant yield and/or increased plant biomass. Genetically modified plants characterized as having increased yield and methods for producing such plants are also provided.

17 Claims, 6 Drawing Sheets

(2 of 6 Drawing Sheet(s) Filed in Color)

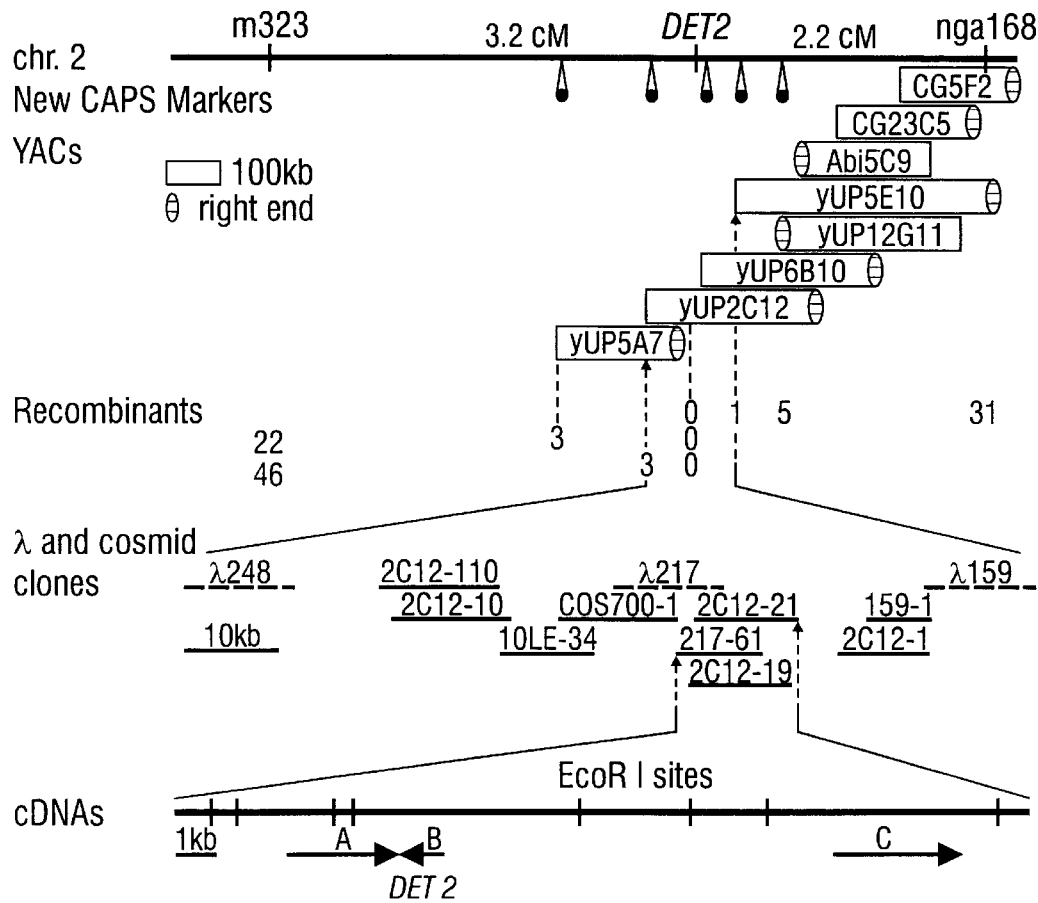
FIC. 1A
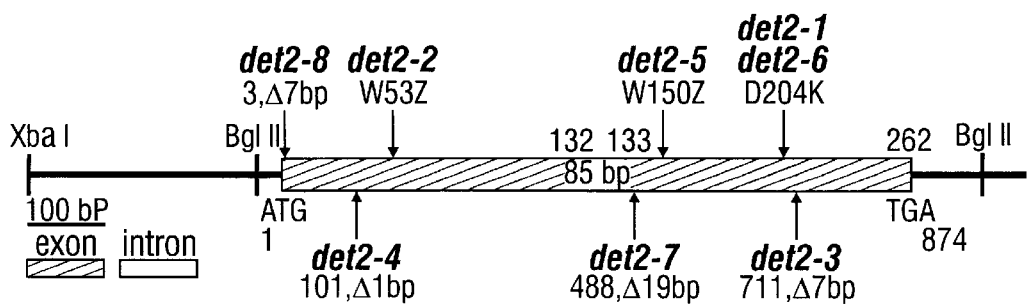
FIC. 1B

DET2 DNA sequence

```
aattccataacccgaaaaatggaagaaatcgccgataaaa
ccttcttccgatactgtcctcactcttattttcgccgg
cccaccaaccgccgtccttctgaattcctccaagctcct
tacggtaaacacaaccgtaccggatggggtcccaccgtat
ctccaccgattgcttggttcgtcatggagagcccaacctt
gtggctcactctcctcctcttcccctttggtcgtcacgct
ctcaaccctaaatctctacttctattctctccttatctca
ttcattacttccaccgccatcatttaccctcttcgcct
cttccgcagctccttccccgccggtaaaaacggatttccg
atcaccatcgccgcttggctttcacctttaatctcctca
atggttatatccaggcgaggtgggtttcgcattacaagga
cgactacgaagacggaaactggttctggtggcggtttgtt
atcggtatggtggttttcataaccggcatgtatataaata
tcacgtcggaccgcactttggtacgattgaagaaagagaa
ccggggaggttatgtgataccgagaggaggctggttcgac
ttggtaagccgtccgaattatttggagaggcgattgagt
ggttgggctgggctgttatgacttggtcttgggccggtat
tggattttctgtacgtgttccaatttgtttccgcgt
gcacgtgcgagtcacaagtggtacattgccaagttcaagg
aagagtatcccaagactcgtaaagctgttattccttttgt
gtactgagaattgagaagttgaaactagtttatcatat
gttatgtgtcaatttgtttccaactaccttttgtcaaaat
ttccagtaaccggtttaattccaacacggtttagatctta
ttagacaaatttta
```

Deduced Protein sequence

```
MEEIADKTFFRYCLLTLIFAGPPTAVLLKFLQAPYGKHNRTGW
GPTVSPPIAWFVMESPTLWLTLLLFPFGRHALNPKSLLLFSPY
LIHYFHRTIIYPLRLFRSSFPAGKNGFPITIAALAFTFNLLNG
YIQARWVSHYKDDYEDGNWFWWRFVIGMVVFITGMYINITSDR
TLVRLKKENRGGYVIPRGGWFELVSRPNYFGEAIEWLGWAVMT
WSWAGIGFFLYTCSNLFPRARASHKWYIAKFKEEYPKTRKAVI
PFVY
```

*FIG. 1C*

PLANT STEROID 5α REDUCTASE, DET2

This invention was made with Government support under Grant No. DIR 9116923 awarded by the National Science Foundation and Grant No. 93-373019125 awarded by the U.S. Department of Agriculture. The Government has certain rights in this invention.

FIELD OF THE INVENTION

The present invention relates generally to plant genetic engineering, and specifically to a novel gene useful for producing genetically engineered plants characterized as having a phenotype of increased crop yield.

BACKGROUND OF THE INVENTION

Plant growth and development are governed by complex interactions between environmental signals and internal factors. Light regulates many developmental processes throughout the plant life cycle, from seed germination to floral induction (Chory, *J. Trends Genet.,* 9:167, 1993; McNellis and Deng, *Plant Cell,* 7:1749, 1995), and causes profound morphological changes in young seedlings. In the presence of light, hypocotyl growth is inhibited, cotyledons expand, leaves develop, chloroplasts differentiate, chlorophylls are produced, and many light-inducible genes are coordinately expressed. It has been suggested that plant hormones, which are known to affect the division, elongation, and differentiation of cells, are directly involved in the response of plants to light signals (P. J. Davies, *Plant Hormones: Physiology, Biochemistry and Molecular Biology*, pp 1–836 , 1995; Greef and Freddericq, Photomorphogenesis, pp 401–427, 1983). The interactions between phototransduction pathways and plant hormones however are not well understood.

The brassinosteroids are a unique class of biologically active natural products that possess high specific activity and plant steroidal hormone activity. Their low effective concentrations for use on crops make them environmentally safe and those brassinosteroids used on a large scale are generally non-toxic. At the physiological level, brassinosteroids elicit many changes and could represent a new class of hormones in plants. The economic aspects of the brassinosteroids may have worldwide effects. The brassinosteroids can be used as plant protectants from both pesticide and environmental adversity. In addition, brassinosteroids appear to be important for insect control. Further, brassinosteroids may regulate some stage of the reproductive cycle in plants, and other species, thereby providing the means to increase or decrease the reproductive process. For example, in certain horticultural crops, it may be desirable to eliminate the flowering process to ensure continuous production of other tissues such as leaves, bulbs and other storage organs. This modulation of the reproductive process could be important in the control of certain seed bearing weeds, where cessation of the flowering cycle eliminates proceeding generations. Brassinosteroids also appear to stimulate root growth, and external application causes no deformity of plants.

Brassinosteroids qualify for classification as biochemical pesticides. Such pesticides are generally distinguished from conventional chemical pesticides by their unique modes of action, low effective concentration, target species, and specificity. Historically, the brassinosteroids have not been used in actual agricultural applications due to the expense involved in producing them as well as the difficulty in purifying them.

SUMMARY OF THE INVENTION

Although steroid hormones are important for animal development, the physiological role of plant steroids is largely unknown. The present invention is based on the discovery of the DET2 gene, which encodes a protein that shares significant sequence identity with mammalian steroid 5α-reductases and is involved in the brassinolide biosynthetic pathway. A mutation of glutamate 204, which is required for the activity of human steroid reductase, abolishes the in vivo activity of DET2 and leads to defects in light-regulated development. These defects can be ameliorated by application of the plant steroid, brassinolide.

In a first embodiment, the invention provides DET2 polypeptide and isolated polynucleotide sequences encoding DET2.

In another embodiment, the invention provides a method for producing a genetically modified plant characterized as having increased yield as compared to a wild-type plant. The method is based on transferring at least one copy of a DET2-encoding polynucleotide operably associated with a promoter to a plant cell to obtain a transformed plant cell and producing a plant from the transformed plant cell. Such genetically modified plants may exhibit increased crop yield or increased biomass, for example.

In yet another embodiment of the invention provides a method for producing a plant characterized as having increased yield by contacting a plant with having a native DET2 gene operably linked to its native promoter, with a promoter-inducing amount of an agent which induces DET2 gene expression, wherein induction of DET2 gene expression results in production of a plant having increased yield as compared to a plant not contacted with the inducing agent. Thus, transcription factors or chemical agents may be used to increase expression of DET2 in a plant, in order to provide increased yield.

BRIEF DESCRIPTION OF THE DRAWINGS

The file of this patent contains at least one drawing executed in color. Copies of this patent with color drawings are provided to the Patent and Trademark Office with payment of the necesary fee.

FIG. 1 is a schematic illustration of the cloning and sequence analysis of the DET2 gene.

FIG. 1A shows a summary of positional cloning. Three classes of cDNA were identified from an Arabidopsis cDNA library with cosmid 217-61 as a probe, and their relative positions and transcriptional directions (5'→3') are indicated.

FIG. 1B shows a map of the gene structure of DET2 and mutations in the DET2 gene. Thick lines indicate exons, and the open box denoted an intron. Positions of mutations are relative to the initiation codon. Z, stop codon.

FIG. 1C shows the nucleotide and deduced amino acid sequence of DET2 (SEQ ID NO:1 and 2, respectively).

FIG. 3 shows a sequence comparison of DET2 with mammalian steroid 5α-reductases.

DESCRIPTION OF THE PREFERRED EMBODIMENTS

Figure 2A:
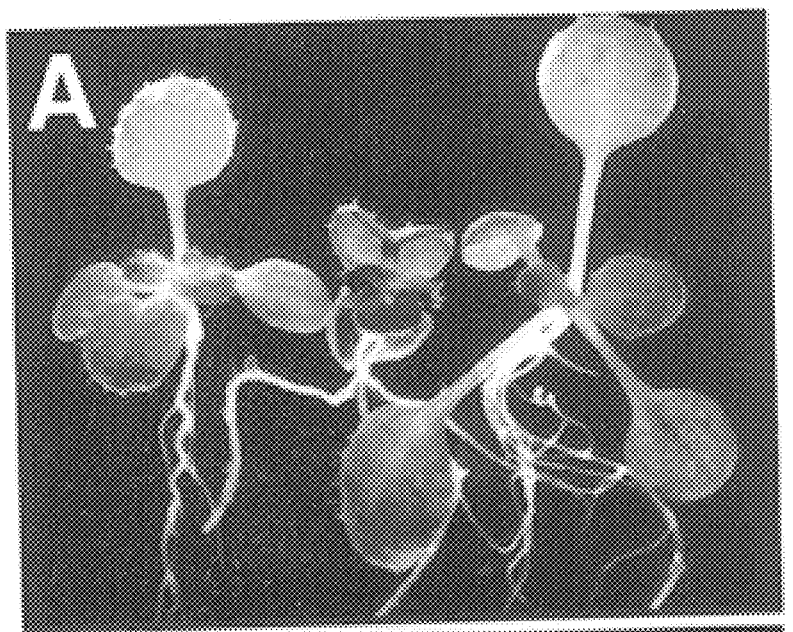
FIG. 2 shows a photo of light-grown 12-day-old seedlings (FIG. 2A) and dark-grown 10-day-old seedlings (FIG. 2B) after complementation of det2 by the wild-type DET2 gene. (From left to right in each panel) Wild-type Col-0, det2-1, and transgenic det2-1 containing cosmid 217-61.

The present invention provides a novel steroid 5α-reductase, DET2, which is involved in the synthesis of the plant steroid hormone, brassinolide. Overexpression of DET2 reductase in transgenic plants causes such plants to become significantly larger and more robust than their wild-type counterparts, thus increasing plant yields.

As used herein, the term "yield" or "plant yield" refers to increased plant growth, increased crop growth, and/or increased biomass production.

In a first embodiment, the present invention provides a substantially pure DET2 polypeptide. DET2 polypeptide is exemplified by the amino acid sequence shown in FIG. 1C and SEQ ID NO:2. DET2 polypeptide is characterized as having a predicted molecular weight of 31 kDa as determined by SDS-PAGE, having steroid 5α reductase activity and functioning in the brassinolide biosynthetic pathway.

The deduced amino acid sequence of the DET2 gene is similar to that of mammalian steroid 5α-reductases, with 38 to 42% sequence identity. The sequence similarity increases to 54 to 60% when conservative substitutions are taken into account. Two isozymes (types 1 and 2) of steroid 5α-reductase have been isolated in rats and humans (Wilson, et al., *Endocr. Rev.*, 14:577, 1993; Russell and Wilson, *Annu. Rev. Biochem.*, 63:25, 1994). Phylogenetic analysis shows that DET2 is at least as closely related to type 2 enzymes as type 2 enzymes are related to type 1 enzymes.

The term "substantially pure" as used herein refers to DET2 polypeptide which is substantially free of other proteins, lipids, carbohydrates or other materials with which it is naturally associated. One skilled in the art can purify DET2 using standard techniques for protein purification. The substantially pure polypeptide will yield a single major band of about 31 kD on a denaturing polyacrylamide gel. The purity of the DET2 polypeptide can also be determined by amino-terminal amino acid sequence analysis.

The invention includes functional DET2 polypeptide, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of DET2 polypeptide", refers to all fragments of DET2 that retain DET2 activity, e.g., steroid 5α-reductase activity. Biologically functional fragments, for example, can vary in size from a polypeptide fragment as small as an epitope capable of binding an antibody molecule to a large polypeptide capable of participating in the characteristic induction or programming of phenotypic changes within a cell.

The steroid 5α-reductase activity of DET2 and the role of in the brassinolide biosynthetic pathway can be utilized in bioassays to identify biologically active fragments of DET2 polypeptide or related polypeptides. For example, DET2 may catalyze the conversion of campesterol to campestanol, therefore an assay can be performed to detect DET2 enzymatic activity. Inhibitors of DET2 could be used to cause loss of function of DET2 resulting in, for example, male sterile plants, reduced stature, etc. For example, inhibition of DET2 is useful in horticulture for creating dwarf varieties.

Minor modifications of the DET2 primary amino acid sequence may result in proteins which have substantially equivalent activity to the DET2 polypeptide described herein in SEQ ID NO:2 (FIG. 1C). Such modifications may be deliberate, as by site-directed mutagenesis, or may be spontaneous. All of the polypeptides produced by these modifications are included herein as long as the biological activity of DET2 is present, e.g., steroid 5α reductase activity is present to promote increased plant or crop yield and/or biomass. Further, deletion of one or more amino acids can also result in a modification of the structure of the resultant molecule without significantly altering its activity. This can lead to the development of a smaller active molecule which could have broader utility. For example, it may be possible to remove amino or carboxy terminal amino acids required for DET2 activity.

DET2 polypeptide includes amino acid sequences substantially the same as the sequence set forth in SEQ ID NO:2. The term "substantially the same" refers to amino acid sequences that retain the activity of DET2 as described herein, e.g., steroid 5α reductase activity. The DET2 polypeptides of the invention include conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Invention proteins can be analyzed by standard SDS-PAGE and/or immunoprecipitation analysis and/or Western blot analysis, for example. In addition, the in vitro synthesized (IVS) protein assay as described in the present examples can be used to analyze DET2 protein product.

The invention also provides an isolated polynucleotide sequence encoding a polypeptide having the amino acid sequence of SEQ ID NO:2. The DET2 gene has been mapped to a 150-kb interval on Arabidopsis chromosome 2. The DET2 transcript contains a single, long open reading frame that encodes a 262-amino acid protein. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode DET2. It is understood that polynucleotides encoding all or varying portions of DET2 are included herein, as long as they encode a polypeptide with DET2 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription. Moreover, DET2 polynucleotides of the invention include polynucleotides having alterations in the nucleic acid sequence which still encode functional DET2. Alterations in DET2 nucleic acid include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)). and in situ hybridization. Invention polynucleotide sequences also include antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of DET2 polypeptide encoded by such nucleotide sequences retains DET2 steroid 5α reductase activity. A "functional polynucleotide" denotes a polynucleotide which encodes a functional polypeptide as described herein. In addition, the invention also includes a polynucleotide encoding a polypeptide having the biological activity of an amino acid sequence of SEQ ID NO:2 and having at least one epitope for an antibody immunoreactive with DET2 polypeptide.

As used herein, the terms polynucleotides and nucleic acid sequences of the invention refer to DNA, RNA and cDNA sequences.

The polynucleotide encoding DET2 includes the nucleotide sequence in FIG. 1C (SEQ ID NO:1), as well as nucleic acid sequences complementary to that sequence. A complementary sequence may include an antisense nucleotide. When the sequence is RNA, the deoxyribonucleotides A, G, C, and T of FIG. 1C are replaced by ribonucleotides A, G, C, and U, respectively. Also included in the invention are fragments ("probes") of the above-described nucleic acid sequences that are at least 15 bases in length, which is sufficient to permit the probe to selectively hybridize to DNA that encodes the protein of FIG. 1C (SEQ ID NO: 2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated DET2 nucleotide sequences.

Specifically disclosed herein is a cDNA sequence for DET2. FIG. 1C shows the complete cDNA and deduced protein sequences (SEQ ID NO:1 and 2, respectively).

DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of the DET2 sequence encoding the protein in question, can be synthesized chemically. This requires that short, oligopeptide stretches of the amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981). Alternatively, a subtractive library, as illustrated herein is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucl. Acid Res., 11:2325, 1983).

A cDNA expression library, such as lambda gt11, can be screened indirectly for DET2 peptides using antibodies specific for DET2. Such antibodies can be either polyclonally or monoclonally derived and used to detect expression product indicative of the presence of DET2 cDNA.

DNA sequences encoding DET2 can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the DET2 polynucleotide sequences may be inserted into a recombinant expression vector. The terms "recombinant expression vector" or "expression vector" refer to a plasmid, virus or other vehicle known in the art that has been manipulated by insertion or incorporation of the DET2 genetic sequence. Such expression vectors contain a promoter sequence which facilitates the efficient transcription of the inserted DET2 sequence. The expression vector typically contains an origin of replication, a promoter, as well as specific genes which allow phenotypic selection of the transformed cells.

Methods which are well known to those skilled in the art can be used to construct expression vectors containing the DET2 coding sequence and appropriate transcriptional/translational control signals. These methods include in vitro recombinant DNA techniques, synthetic techniques, and in vivo recombination/genetic techniques.

A variety of host-expression vector systems may be utilized to express the DET2 coding sequence. These include but are not limited to microorganisms such as bacteria transformed with recombinant bacteriophage DNA, plasmid DNA or cosmid DNA expression vectors containing the DET2 coding sequence; yeast transformed with recombinant yeast expression vectors containing the DET2 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the DET2 coding sequence; insect cell systems infected with recombinant virus expression vectors (e.g., baculovirus) containing the DET2 coding sequence; or animal cell systems infected with recombinant virus expression vectors (e.g., retroviruses, adenovirus, vaccinia virus) containing the DET2 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted DET2 coding sequence.

Isolation and purification of recombinantly expressed polypeptide, or fragments thereof, provided by the invention, may be carried out by conventional means including preparative chromatography and immunological separations involving monoclonal or polyclonal antibodies.

The invention also includes antibodies immunoreactive with DET2 polypeptide or antigenic fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975).

The term "antibody" as used in this invention includes intact molecules as well as fragments thereof, such as Fab, F(ab')2, and Fv which are capable of binding to an epitopic determinant present in DET2 polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" refers. to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the DET2 polypeptide of the invention can be prepared using an intact polypeptide or fragments containing small peptides of interest as the immunizing antigen. For example, it may be desirable to produce antibodies that specifically bind to the N- or C-terminal domains of DET2. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

In another embodiment, the invention provides a method for producing a genetically modified plant characterized as having increased yield as compared to a plant which has not been genetically modified (e.g., a wild-type plant). The term "yield" has been previously defined herein. The method includes the steps of contacting a plant cell with at least one vector containing at least one nucleic acid sequence encoding DET2, wherein the nucleic acid sequence is operably associated with a promoter, to obtain a transformed plant cell; producing a plant from the transformed plant cell; and thereafter selecting a plant exhibiting increased yield.

The term "genetic modification" as used herein refers to the introduction of one or more heterologous nucleic acid sequences, e.g., DET2 encoding sequence, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, etc.

The term "heterologous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In the broad method of the invention, at least one nucleic acid sequence encoding DET2 is operably linked with a promoter. It may be desirable to introduce more than one copy of DET2 polynucleotide into a plant for enhanced DET2 expression. For example, multiple copies of the gene would have the effect of increasing production of DET2 in the plant.

Genetically modified plants of the present invention are produced by contacting a plant cell with a vector including at least one nucleic acid sequence encoding DET2. To be effective once introduced into plant cells, the DET2 nucleic acid sequence must be operably associated with a promoter which is effective in the plant cells to cause transcription of DET2. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non-transformed cells in culture, as described herein.

The term "operably associated" refers to functional linkage between a promoter sequence and the DET2 nucleic acid sequence regulated by the promoter. The operably linked promoter controls the expression of the DET2 nucleic acid sequence.

The expression of structural genes employed in the present invention may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., *Nature*, 310:511, 1984; Odell, et al., *Nature*, 313:810, 1985); the full-length transcript promoter from Figwort Mosaic Virs (FMV) (Gowda, et al., *J. Cell Biochem.*, 13D: 301, 1989) and the coat protein promoter to TMV (Takamatsu, et al., *EMBO J.* 6:307, 1987). Alternatively, plant promoters such as the light-inducible promoter from the small subunit of ribulose bis-phosphate carboxylase (ssRUBISCO) (Coruzzi, et al., *EMBO J.*, 3:1671, 1984; Broglie, et al., *Science*, 224:838, 1984); mannopine synthase promoter (Velten, et al., *EMBO J.*, 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., *Mol. Cell. Biol.*, 6:559, 1986; Severin, et al., *Plant Mol. Biol.*, 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.*, 90:4567, 1993); In2-1 and In2-2 regulator sequences which are activated by substituted benzenesulfonamides, e.g., herbicide safeners (Hershey, et al., *Plant Mol. Biol.*, 17:679, 1991); and the GRE regulatory sequences which are induced by glucocorticoids (Schena, et al., *Proc. Natl. Acad. Sci., U.S.A.*, 88:10421, 1991). Other promoters, both constitutive and inducible will be known to those of skill in the art.

The particular promoter selected should be capable of causing sufficient expression to result in the production of an effective amount of structural gene product, e.g., DET2, to cause increased yield and/or increased biomass. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al., *Plant J.*, 2:291, 1992). Other tissue specific promoters useful in transgenic plants, including the cdc2a promoter and cyc07 promoter, will be known to those of skill in the art. (See for example, Ito, et al., *Plant Mol. Biol.*, 24:863, 1994; Martinez, et al., *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al., *Plant Journal*, 4:411, 1993).

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phosphoribosyltransferase and amino-glycoside 3'-O-phosphotransferase II (kanamycin, neomycin and G418 resistance). Other suitable markers will be known to those of skill in the art.

Vector(s) employed in the present invention for transformation of a plant cell include a nucleic acid sequence encoding DET2, operably associated with a promoter. To commence a transformation process in accordance with the present invention, it is first necessary to construct a suitable vector and properly introduce it into the plant cell. Details of the construction of vectors utilized herein are known to those skilled in the art of plant genetic engineering.

DET2 nucleic acid sequences utilized in the present invention can be introduced into plant cells using Ti plasmids of Agrobacterium tumefaciens, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., *Science,* 227:1229, 1985, both incorporated herein by reference). In addition to plant transformation vectors derived from the Ti or root-inducing (Ri) plasmids of Agrobacterium, alternative methods may involve, for example, the use of liposomes, electroporation, chemicals that increase free DNA uptake, transformation using viruses or pollen and the use of microprojection.

One of skill in the art will be able to select an appropriate vector for introducing the DET2-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of DET2 nucleic acid sequence.

For example, a DET2 nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology,* 1: 262, 1983; Hoekema, et al., *Nature,* 303:179, 1983). Such a binary system is preferred because it does not require integration into the Ti plasmid of Agrobacterium, which is an older methodology.

Methods involving the use of Agrobacterium in transformation according to the present invention include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold, et al., (*C. R. Acad. Sci. Paris,* 316:1194, 1993) and exemplified in the Examples herein. This approach is based on the vacuum infiltration of a suspension of Agrobacterium cells.

The preferred method of introducing DET2-encoding nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, DET2 encoding nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

DET2 nucleic acid sequences can also be introduced into plant cells by electroporation (Fromm, et al., *Proc. Natl. Acad. Sci., U.S.A.,* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing DET2 nucleic acid into a plant cell is high velocity ballistic penetration by small particles with the nucleic acid to be introduced contained either within the matrix of such particles, or on the surface thereof (Klein, et al., *Nature* 327:70, 1987). Bombardment transformation methods are also described in Sanford, et al. (*Techniques* 3:3–16, 1991) and Klein, et al. (*Bio/Techniques* 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing DET2 into the plant cell, including chemical and physical means as described above. Preferably, contacting refers to introducing the nucleic acid or vector into plant cells (including an explant, a meristem or a seed), via *Agrobacterium tumefaciens* transformed with the DET2 encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee, et al., *Annual Review of Plant Physiology*, 38:467, 1987). Utilizing the leaf disk-transformation-regeneration method of Horsch, et al., *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g. increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting increased yield or biomass as compared with wild-type plants can be selected by visual observation. The invention includes plants produced by the method of the invention, as well as plant tissue and seeds.

In yet another embodiment, the invention provides a method for producing a genetically modified plant cell such that a plant produced from said cell produces increased yield as compared with a wild-type plant. The method includes contacting the plant cell with a DET2 nucleic acid sequence to obtain a transformed plant cell; growing the transformed plant cell under plant forming conditions to obtain a plant having increased yield. Conditions such as environmental and promoter inducing conditions vary from species to species, but should be the same within a species.

In another embodiment, the invention provides a method of producing a plant characterized as having increased yield by contacting a susceptible plant with a DET2 promoter-inducing amount of an agent which induces DET2 gene expression, wherein induction of DET2 gene expression results in production of a plant having increased yield as compared to a plant not contacted with the agent.

A "susceptible plant" refers to a plant that can be induced to utilize its endogenous DET2 gene to achieve increased yield. The term "promoter inducing amount" refers to that amount of an agent necessary to elevate DET2 gene expression above DET2 expression in a plant cell not contacted with the agent. For example, a transcription factor or a chemical agent may be used to elevate gene expression from DET2 native promoter, thus inducing the promoter and DET2 gene expression.

In another aspect of the invention, it is envisioned that increased expression of DET2 in a plant cell or in a plant, increases resistance of that cell/plant to plant pests or plant pathogens. For example, field studies have shown that brassinolides are effective as pesticides, therefore, increased expression of DET2 would result in increased amounts of brassinolide in the plant. In addition, increased DET2 expression may also cause increased resistance to pesticides (safeners). DET2 therefore, protects plants against pests as well as against pesticides.

The above disclosure generally describes the present invention. A more complete understanding can be obtained by reference to the following specific examples which are provided herein for purposes of illustration only and are not intended to limit the scope of the invention.

EXAMPLES

Previously, Arabidopsis mutants that have characteristics of light-grown plants even when grown in the dark have been isolated. At least 11 such gene loci, known as det, cop, and fus, have been identified (Bowler and Chua, *Plant Cell*, 6:1529, 1994). Double-mutant analyses with several photo-receptor mutants suggest that DET1, COP1, and COP9 act in one signal transduction pathway, whereas DET2 acts in a different pathway (Bowler and Chua, supra). DET1, COP1, and COP9 all encode nuclear-localized proteins whose mode of action is not yet understood (Bowler and Chua, supra).

Loss-of-function mutations in DET2 have pleiotropic effects (Chory, et al., ibid, 3:445, 1991). In the dark, det2 mutants are short, have thick hypocotyls, accumulate anthocyanins, have open, expanded cotyledons, and develop primary leaf buds. These morphological changes are accompanied by a 10-to 20-fold derepression of several light-responsive genes. In the light, det2 mutants are smaller and darker green than wild type, show reduced cell size in the tissues examined (hypocotyl, cotyledons, and leaves), and have reduced apical dominance and male fertility. det2 mutations also affect photoperiodic responses and cause a delay in flowering, a shortening of the circadian period of CAB (chlorophyl a/b-binding proteins) gene expression, inappropriate day and night regulation of gene expression, and a delay of leaf and chloroplast senescence (Chory, et al., supra; Chory, et al., *Plant physiol.*, 104:339, 1994; Millar, et al., Science, 267:1163, 1995). Such phenotype differences show that DET2 plays an important role throughout Arabidopsis development.

Example 1

The DET2 gene was mapped to a 150-kb interval on Arabidopsis chromosome 2 (FIG. 1A). FIG. 1 is a schematic illustration of the cloning and sequence analysis of the DET2 gene. FIG. 1A shows a summary of positional cloning. Homozygous det2-1 mutant (Col-0) was crossed to either wild-type No-0 or La-er (geographic isolate designations).

DNA from $F_2$ det2 seedings was prepared (Deilaporta, et al., *Plant Mol. Biol. Rep.*, 1:19, 1983) for simple sequence length polymorphisms (SSLPs) (Bell and Ecker, Genomic, 19:137, 1994) and cleaved amplified polymorphic sequences (CAPS)(Konieczny and Ausubel, *Plant J.*, 4:403, 1993). Overlapping yeast artificial chromosome (YAC) clones were isolated from three separate YAC libraries of Arabidopsis (Ward and Jen, *Plant Mol. Biol.*, 14:561, 1990; J. R. Ecker, Methods, 1:186, 1990; Grill and Somerville, *Mol. Gen. Genet.*, 226:484, 1991) Fine-RFLP analysis was performed with $F_2$ det2 plants with recombination break points either in the m323-DET2 region (68 recombinants, two mapping populations) or in the DET2-nga 168 interval (31 recombinants).

Molecular marker ngal68 was used as the starting point for identifying eight overlapping YAC clones covering ~800 kb of Arabidopsis genomic DNA. New CAPS markers were converted directly from YAC insert ends or derived from phage clones of an Arabidopsis genomic library isolated with YAC end probes. RFLP analysis delimited the DET2 locus to a 150 ~kb region between the left ends of yUP2C12 and yUPSE10 in Arabidopsis chromosome 2.

A cosmid contig was assembled within this region from cosmid and phage clones isolated from two Arabidopsis genomic libraries (Olszewski, et al., *Nucleic Acids Res.*, 16:10765, 1988) by hybridization with yUP2C12, yUP6B10, YAC end probes, or cosmid-derived probes.

Figure 2B:
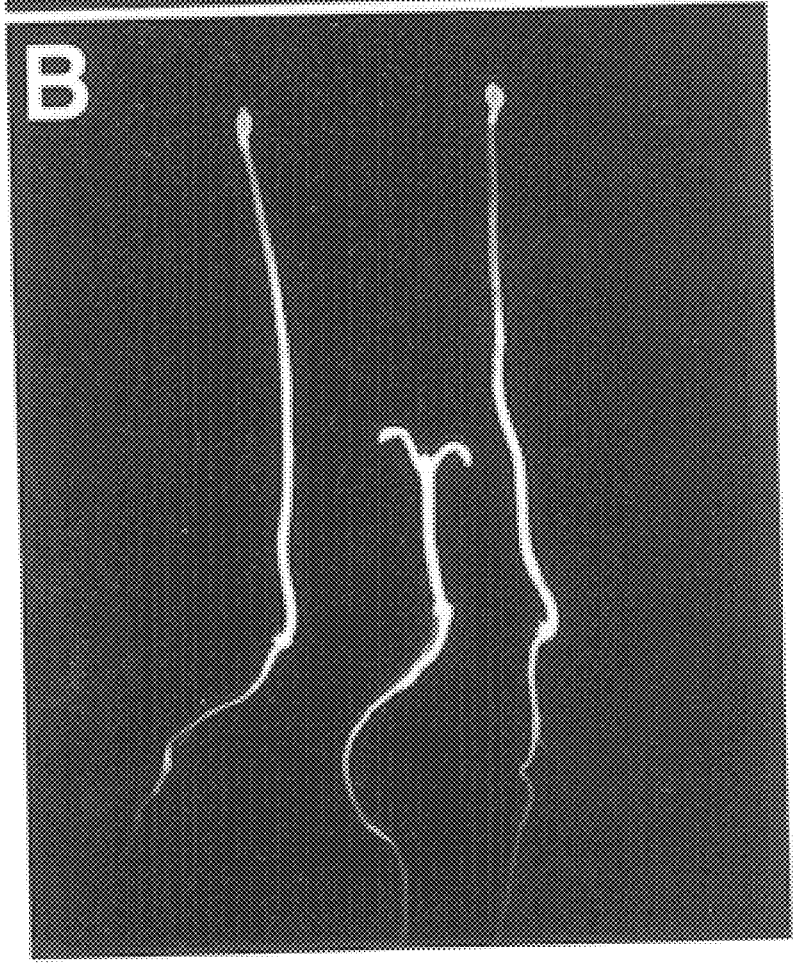

Cosmid DNAs were transformed into det2-1 plants by a modified vacuum infiltration method (Bechtold, et al.,*Acad. Sci. Paris*, 316:1194, 1993; Bent, et al., *Science,* 265:1856, 1994) to identify cosmids containing the DET2 gene. Three cosmids, 2C12-19, 2C12-21, and 217-61, rescued det2 mutant phenotypes. A 20-kb genomic fragment was identified that can rescue the det2 phenotypes. FIG. 2 shows a photo of light-grown 12-day-old seedlings (FIG. 2A) and dark-grown 10-day-old seedlings (FIG. 2B) after complementation of det2 by the wild-type DET2 gene. (From left to right in each panel) Wild-type Col-0, det2-1, and transgenic det2-1 containing cosmid 217-61. Labeled Eco R1 fragments of cosmid 217-61 were used as probes to screen ~2×10$^6$ clones of an Arabidopsis complementary DNA (cDNA) library constructed in lambda ZAPII (Kieber, et al., *Cell,* 72:427, 1993). Positive clones were converted to plasmids by in vivo excision according to the manufacturer's protocol (Stratagene) and sequenced with gene-specific primers. The 20 kb fragment gives rise to at least three transcripts (FIG. 1A), one of which is altered in all det2 alleles analyzed and is derived from the DET2 gene (FIG. 1B).

The DET2 transcript contains a single, long open reading frame that encodes a 262-amino acid protein. The corresponding genomic sequences of eight det2 alleles, all which have similar mutant phenotypes, were determined. The transcribed region of the DET2 gene was amplified by polymerase chain reaction (PCR) from genomic DNAs of wild-type Col-0 and eight det2 alleles, subcloned into PGEM-T vector (Promega), and sequenced. To minimize PCR errors, at least four different clones from two independently amplified fragments were pooled for sequencing. Four alleles contain frame shifting deletions, and another two mutations cause premature termination of the DET2 protein. The two remaining alleles have a nonconservative substitution of lysine for glutamate at position 204 (FIG. 1B). FIG. 1B shows a map of the gene structure of DET2 and mutations in the DET2 gene. Thick lines indicate exons, and the open box denotes an intron. Positions of mutations are relative to the initiation codon. Z, stop codon. FIG. 1C shows the nucleotide and deduced amino acid sequence of DET2 (SEQ ID NO:1 and 2, respectively).

Figure 3A:
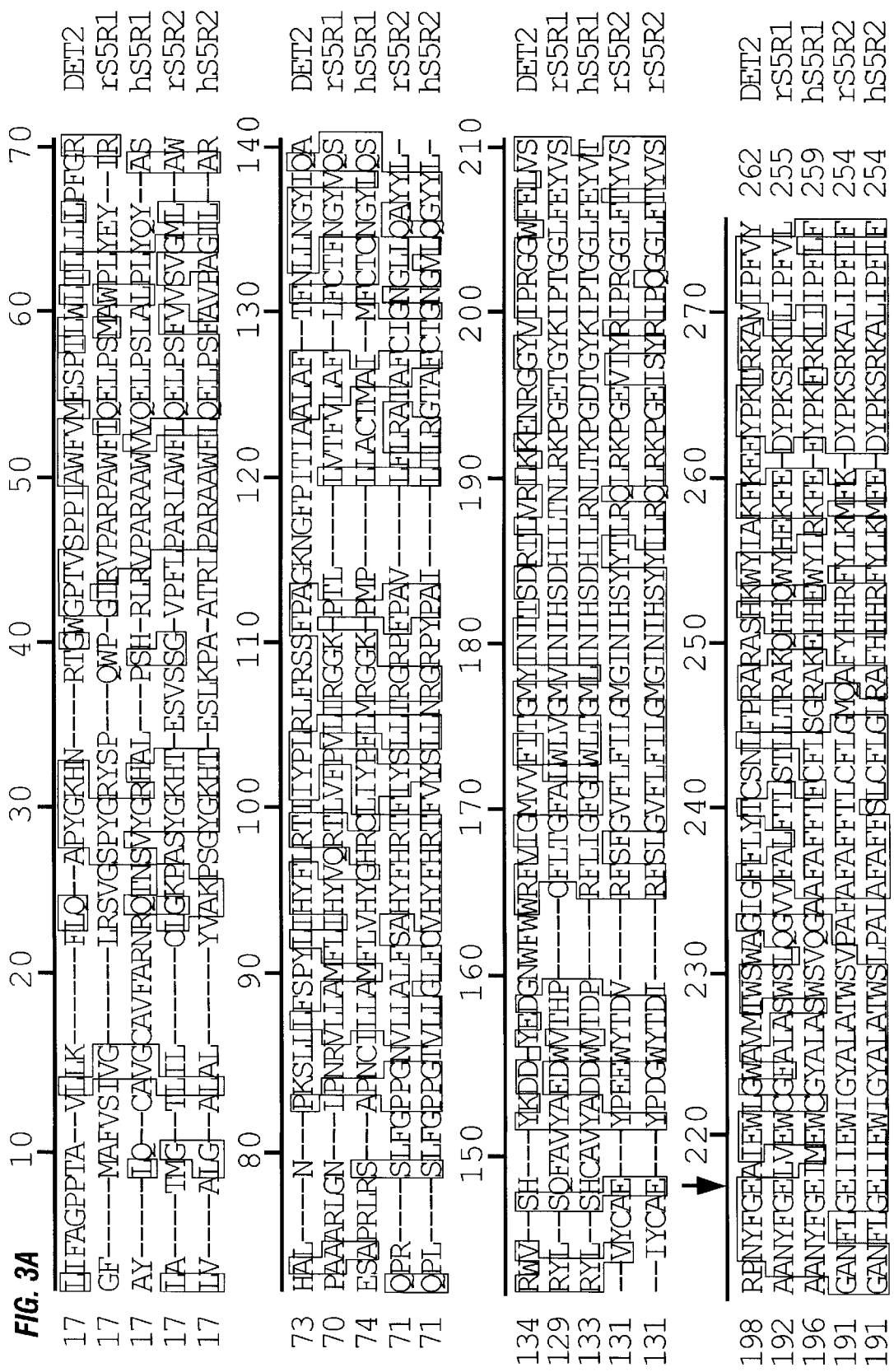
FIG. 3A is the deduced amino acid sequence of the DET2 gene aligned with the steroid 5α-reductases from rat (rS5R1 and rS5R2) and human (hS5R1 and hS5R2). Dashes indicate gaps introduced to maximize alignment, and residues conserved in at least two of the five sequences are shaded. The arrow indicates the glutamate mutated in det2-1 and det2-6 alleles. (Single-letter abbreviation for the amino acid residues are as follows: A, Alta; C, Cys; D, Asp; E, Glu; F, Phe; G, Gly; H, His; I, Ile; K, Lys; L, Leu; M, Met; N, Asn; P, Pro; Q, Gin; R, Arg; S, Ser; T, The; V, Val; W, Trp; and Y, Tyr).
Figure 3B:
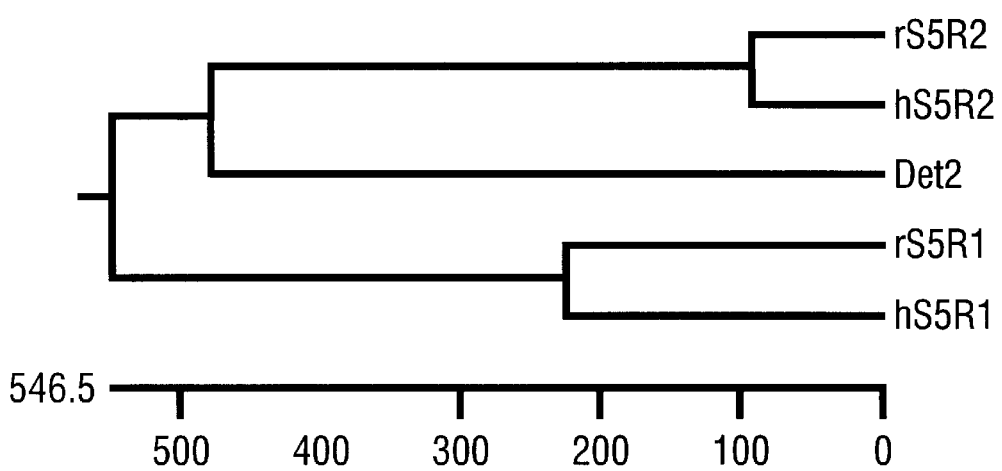
FIG. 3B shows a phylogenetic analysis of the relationship between DET2 protein and mammalian steroid 5α-reductases. The scale measures the relative distance between sequences.

FIG. 3 shows a sequence comparison of DET2 with mammalian steroid 5α-reductases. FIG. 3A shows the deduced amino acid sequence of the DET2 gene aligned with the steroid 5α-reductases from rat (rS5R1 and rS5R2) and human (hS5R1 and hS5R2). Dashes indicate gaps introduced to maximize alignment, and residues conserved in at least two of the five sequences are shaded. Arrow indicates the glutamate mutated in det2-1 and det2-6 alleles. (Single-letter abbreviation for the amino acid residues are as follows: A, Alta; C, Cys; D, Asp; E, Glu; F, Phe; G, Gly; H, His; I, Ile; K, Lys; L, Leu; M, Met; N, Asn; P, Pro; Q, Gin; R, Arg; S, Ser; T, The; V, Val; W, Trp; and Y, Tyr). FIG. 3B shows a phylogenetic analysis of the relationship between DET2 protein and mammalian steroid 5α-reductases. The scale measures the relative distance between sequences.

The deduced amino acid sequence of the DET2 gene is similar to that of mammalian steroid 5α-reductases, with 38 to 42% sequence identity. (Database searches were performed at the U.S. National Center for Biotechnology information with the BLAST program (Altschul, et al., *J. Mol. Biol.,* 215:403, 1990). Sequence alignment and phylogenetic analysis were performed with the Megalign program (DNAStar) by the method of J. Hein (Higgins and Sharp, *Comput. Appl. Biosci.,* 5:151, 1989)). The sequence similarity increases to 54 to 60% when conservative substitutions are taken into account. Two isozymes (types 1 and 2) of steroid 5α-reductase have been isolated in rats and human (Wilson, et al., *Endocr. Rev.,* 14:577, 1993; Russell and Wilson, *Annu. Rev. Biochem.,* 63:25, 1994). Phylogenetic analysis shows that DET2 is at least as closely related to type 2 enzymes as type 2 enzymes are related to type 1 enzymes (FIG. 3B).

Eighty percent of the absolutely conserved residues in mammalian enzymes are found in the predicted DET2 protein. Mammalian steroid 5α-reductases catalyze the nicotinamide adenine dinucleotide phosphate (reduced) (NADPH)-dependent conversion of testosterone to dihydrotestosterone, which is a key step in steroid metabolism and is essential for the embryonic development of male external genitalia and prostate (Wilson, et al., supra). The importance of this reaction is evident from certain hereditary forms of male pseudohermaphroditism in humans caused by steroid 5α-reductase deficiency. Sequences analysis of the steroid 5α-reductase type 2 gene from affected families identifies a missense mutation that causes a conservative substitution of aspartate for Glu$^{197}$ (Wilson, et al., supra), corresponding to Glu$^{204}$ in DET2. In the det2-1 and det2-6 alleles, this glutamate is changed to lysine, indicating that this glutamate has a similar critical function as in the human 5α-reductase. Because a conservative substitution at this position causes inactivation of the human enzyme (Wilson, et al., supra), that the non-conservative glutamate-to-lysine change is predicted to completely abolish DET2 activity. This could explain the severe phenotypes of the two missense alleles. Taken together, the data suggest that the DET2 enzyme may catalyze a biochemical reaction similar to the reaction catalyzed by the human enzyme.

Example 2

In plants, many steroids have been identified (J. M. C. Geuns, *Phytochemistry,* 17:1, 1978), but only brassinosteroids (BRs) have wide distribution throughout the plant kingdom and unique biological activity on plant growth when applied exogenously (N. B. Mandava, *Annu. Rev. Plant Physiol. Plant Mol. Biol.,* 39:23, 1988; R. N. Arteca, (2), 206–213). A pathway for the biosynthesis of brassinolide, the most active BR, has recently been proposed on the basis of evidence from cell suspension cultures and whole-seeding experiments(Fujioka, et al.,*Bio. Sci. Biotechnical. Biochem.,* 59:1973, 1995). Although the biosynthesis of brassinolide involves many oxidation steps, only two steps involve reduction. One occurs early in the pathway where a double bond in campesterol is reduced to form campestanol. This reaction is similar to that catalyzed by mammalian steroid 5α-reductases, suggesting that DET2 could catalyze the conversion of campesterol to campestanol. Because the Arabidopsis genome does not contain any other sequences that are closely related to DET2, one possibility is that the det2 phenotype is due to reduction or elimination of BR biosynthesis.

Figure 4A:
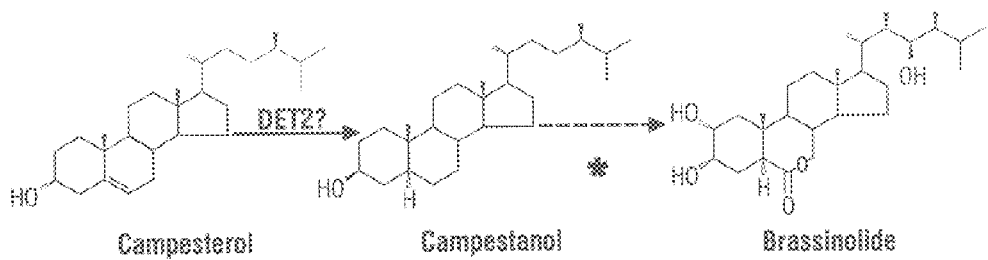
FIG. 4A shows the proposed function of DET2 protein in the brassinolide biosynthetic pathway. Asterisk (*) indicates six intermediate steps (Fujicka, et al., supra).
Figures 4B, 4C:
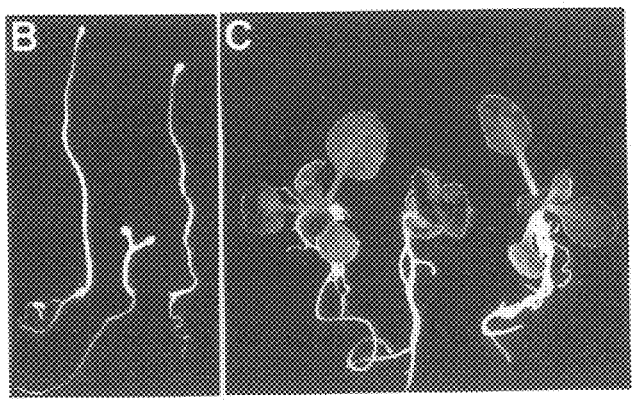
FIG. 4B shows dark-grown 10-day-old Arabadopsis seedlings.
FIG. 4C shows light-grown 12-day-old seedlings. Shown from left to right in each panel are wild-type, det2-1, and brassinolide-treated det2-1 plants.
Figure 4D:
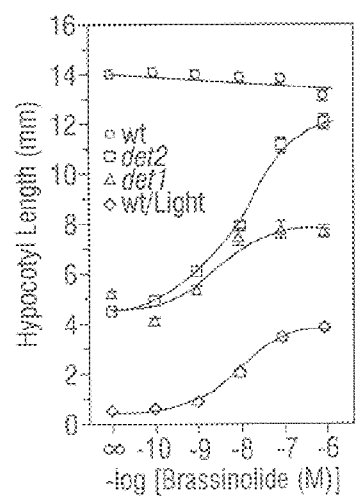
FIG. 4D shows a dose-response of brassinolide-induced hypocotyl elongation of dark-grown seedlings and light-grown wild-type plants. Data represent the mean ± SE obtained from triplicate determinations, each with an average sample size of 12 seedlings.

To test this hypothesis, det2 seedlings were treated with exogenous brassinolide. FIG. 4A shows the proposed function of DET2 protein in the brassinolide biosynthetic pathway. Asterisk (*) indicates six intermediate steps (Fujicka, et al., supra). FIG. 4B shows dark-grown 10-day-old seedlings and FIG. 4C light-grown 12-day-old seedlings. Wild-type, det2-1, and brassionolide-treated det2-1 plants are depicted from left to right in each panel. Seeds were germinated on moist Whatman papers placed on MS medium (0.5×MS salts(Gibco), 1× Gamborg's B5 vitamins (Sigma), 0.8% phytagar, and 1 sucrose pH 5.7) for 2 days and transferred to fresh plates supplemented with various concentrations of auxin (IAA, 0 to $10^{-5}$ M), brassinolide (0 to $10^{-6}$ M), and gibberellins (GA1 and GA4, 0 to $10^{-5}$ M). Hormones were sterile-filtered into the cooling MS medium. For dark-grown seedlings, seeds were exposed to 2-hour light treatment before their plates were wrapped with three layers of aluminum foil and the seedlings were transferred under a green safe-light. The hypocotyl lengths of 10-day-old etiolated seedlings and 12-day-old light-grown wild-type plants were measured.). FIG. 4D shows a dose-response of brassinolide-induced hypocotyl elongation of dark-grown seedlings and light-grown wild-type). Data represent the mean ± SE obtained from triplicate determinations, each with an average sample size of 12 seedlings.

Although addition of brassinolide at $10^{-6}$ M to the growth medium had no effect on wild-type seedlings in the dark, the short hyocotyl phenotype of dark-grown det2 seedlings was rescued (FIG. 4, B and D). Similarly when added at $10^{-7}$ M, brassinolide had no effect on the petioles and leaves of wild-type seedlings but fully suppressed the dwarf phenotypes of these organs in light-grown det2 plants (FIG. 4C). In contrast, neither applied gibberellins (GA1 or GA4, $10^{-8}$ to $10^{-5}$ M) nor auxins (1A, A $10^{-6}$ and $10^{-5}$ M) rescued the det2 defects. Brassinolide treatment reversed the inhibition of hypocotyl elongation caused either by det1 mutation or light (FIG. 4D), but it did not complement the mutant phenotypes of either dark-or light-grown det1 seedlings, supporting previous genetic studies that DET1 and DET2 act on separate pathways controlling light-regulated processes.

Although the invention has been described with reference to the presently preferred embodiments, it should be understood that various modifications can be made without departing from the spirit of the invention. Accordingly, the invention is limited only by the following claims.

What is claimed is:

1. An isolated polynucleotide encoding an amino acid sequence as set forth in SEQ ID NO:2.

2. An isolated polynucleotide according to claim 1 having a nucleotide sequence as set forth in SEQ ID NO:1, or variations thereof which encode the same amino acid sequence, but employ different codons for some of the amino acids, or splice variant nucleotide sequences thereof.

3. A recombinant expression vector comprising a polynucleotide sequence according to claim 1.

4. A host cell comprising the vector of claim 3.

5. A method of producing a genetically modified plant characterized as having increased yield as compared to a wild-type plant, said method comprising:
   contacting a plant cell with at least one nucleic acid sequence encoding DET2, said nucleic acid sequence operably associated with a promoter, to obtain a transformed plant cell;
   producing a plant from said transformed plant cell; and
   selecting a plant exhibiting said increased yield.

6. The method of claim 5, wherein the contacting is by physical means.

7. The method of claim 5, wherein the contacting is by chemical means.

8. The method of claim 5, wherein the plant cell is selected from the group consisting of protoplasts, gamete producing cells, and cells which regenerate into whole plants.

9. The method of claim 5, wherein the promoter is selected from the group consisting of a constitutive promoter and an inducible promoter.

10. A plant produced by the method of claim 5.

11. Plant tissue derived from a plant produced by the method of claim 5.

12. A seed derived from a plant produced by the method of claim 5.

13. A method for genetically modifying a plant cell such that a plant, produced from said cell produces increased yield as compared with a wild-type plant, said method comprising:
   contacting said plant cell with the polynucleotide of claim 1 to obtain a transformed plant cell; and
   growing the transformed plant cell under plant forming conditions to obtain a plant having increased yield.

14. The method of claim 13, wherein inducing increased growth is achieved by inducing expression of a polynucleotide of claim 5 in the plant.

15. A method of producing a plant characterized as having increased yield, said method comprising:

contacting a susceptible plant with a DET2 promoter-inducing amount of exogenous brassinolide necessary to elevate DET2 gene expression above DET2 expression in a plant not contacted with the agent.

16. The polynucleotide of claim 1, wherein the polynucleotide encodes an amino acid sequence as set forth in SEQ ID NO:2.

17. An isolated polynucleotide selected from the group consisting of:

a) SEQ ID NO: 1;

b) SEQ ID NO: 1, wherein T can also be U;

c) nucleic sequences complementary to SEQ ID NO:1; and d) fragments of a), b), or c), that are at least 15 bases in length and that selectively hybridize to DNA which encodes the polypeptide of SEQ ID NO:2.

* * * * *

UNITED STATES PATENT AND TRADEMARK OFFICE
CERTIFICATE OF CORRECTION

PATENT NO. : 6,143,950
DATED : November 7, 2000
INVENTOR(S) : Chory et al.

Page 1 of 1

It is certified that error appears in the above-identified patent and that said Letters Patent is hereby corrected as shown below:

Column 28,
Line 65, claim 14 should read:
-- The method of claim 13, wherein inducing increased growth is achieved by inducing expression of a polynucleotide of claim 1 in the plant. --

Signed and Sealed this

Eleventh Day of June, 2002

*Attest:*

JAMES E. ROGAN
*Director of the United States Patent and Trademark Office*

*Attesting Officer*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 974 base pairs
       (B) TYPE: nucleic acid
       (C) STRANDEDNESS: single
       (D) TOPOLOGY: linear (xi) SEQUENCE DESCRIPTION: SEQ ID NO:1:

```
AATTCCATAA CCCGAAAAAT GGAAGAAATC GCCGATAAAA CCTTCTTCCG ATACTGTCTC      60

CTCACTCTTA TTTTCGCCGG CCCACCAACC GCCGTCCTTC TGAAATTCCT CCAAGCTCCT     120

TACGGTAAAC ACAACCGTAC CGGATGGGGT CCCACCGTAT CTCCACCGAT TGCTTGGTTC     180

GTCATGGAGA GCCCAACCTT GTGGCTCACT CTCCTCCTCT TCCCCTTTGG TCGTCACGCT     240

CTCAACCCTA AATCTCTACT TCTATTCTCT CCTTATCTCA TTCATTACTT CCACCGCACC     300

ATCATTTACC CTCTTCGCCT CTTCCGCAGC TCCTTCCCCG CCGGTAAAAA CGGATTTCCG     360

ATCACCATCG CCGCCTTGGC TTTCACCTTT AATCTCCTCA ATGGTTATAT CCAGGCGAGG     420

TGGGTTTCGC ATTACAAGGA TGACTACGAA GACGAAACT GGTTCTGGTG GCGGTTTGTT      480

ATCGGTATGG TGGTTTTCAT AACCGGCATG TATATAAATA TCACGTCGGA CCGCACTTTG     540

GTACGATTGA AGAAAGAGAA CCGGGGAGGT TATGTGATAC CGAGAGGAGG CTGGTTCGAG     600

TTGGTAAGCC GTCCGAATTA TTTTGGAGAG GCGATTGAGT GGTTGGGCTG GGCTGTTATG     660

ACTTGGTCTT GGGCCGGTAT TGGATTTTTT CTGTACACGT GTTCCAATTT GTTTCCGCGT     720

GCACGTGCGA GTCACAAGTG GTACATTGCC AAGTTCAAGG AAGAGTATCC CAAGACTCGT     780

AAAGCTGTTA TTCCTTTTGT GTACTGAGAA TTGAGAAAGT TGAAAACTAG TTTATCATAT     840

GTTATGTGTC AATTTGTTTC CAAACTACCT TTGTCAAAAT TTCCAGTAAC CGGTTTAATT     900
```

```
CCAACACGGT TTAGATCTTA TGTTGGTATC TTCAACAATG CACAACAAAC TGTGTATTCT      960

TTAGACAAAT TTTA                                                        974
```

(2) INFORMATION FOR SEQ ID NO:2:

(i) SEQUENCE CHARACTERISTICS:
        (A) LENGTH: 262 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

```
Met Glu Glu Ile Ala Asp Lys Thr Phe Phe Arg Tyr Cys Leu Leu Thr
1               5                   10                  15

Leu Ile Phe Ala Gly Pro Pro Thr Ala Val Leu Leu Lys Phe Leu Gln
            20                  25                  30

Ala Pro Tyr Gly Lys His Asn Arg Thr Gly Trp Gly Pro Thr Val Ser
        35                  40                  45

Pro Pro Ile Ala Trp Phe Val Met Glu Ser Pro Thr Leu Trp Leu Thr
50                  55                  60

Leu Leu Leu Phe Pro Phe Gly Arg His Ala Leu Asn Pro Lys Ser Leu
65                  70                  75                  80

Leu Leu Phe Ser Pro Tyr Leu Ile His Tyr Phe His Arg Thr Ile Ile
                85                  90                  95

Tyr Pro Leu Arg Leu Phe Arg Ser Ser Phe Pro Ala Gly Lys Asn Gly
            100                 105                 110

Phe Pro Ile Thr Ile Ala Ala Leu Ala Phe Thr Phe Asn Leu Leu Asn
        115                 120                 125

Gly Tyr Ile Gln Ala Arg Trp Val Ser His Tyr Lys Asp Asp Tyr Glu
130                 135                 140

Asp Gly Asn Trp Phe Trp Trp Arg Phe Val Ile Gly Met Val Val Phe
145                 150                 155                 160

Ile Thr Gly Met Tyr Ile Asn Ile Thr Ser Asp Arg Thr Leu Val Arg
                165                 170                 175

Leu Lys Lys Glu Asn Arg Gly Gly Tyr Val Ile Pro Arg Gly Gly Trp
            180                 185                 190

Phe Glu Leu Val Ser Arg Pro Asn Tyr Phe Gly Glu Ala Ile Glu Trp
        195                 200                 205

Leu Gly Trp Ala Val Met Thr Trp Ser Trp Ala Gly Ile Gly Phe Phe
210                 215                 220

Leu Tyr Thr Cys Ser Asn Leu Phe Pro Arg Ala Arg Ala Ser His Lys
225                 230                 235                 240

Trp Tyr Ile Ala Lys Phe Lys Glu Glu Tyr Pro Lys Thr Arg Lys Ala
                245                 250                 255

Val Ile Pro Phe Val Tyr
            260
```

(2) INFORMATION FOR SEQ ID NO:3:

(i) SEQUENCE CHARACTERISTICS:
        (A) LENGTH: 246 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

```
Leu Ile Phe Ala Gly Pro Pro Thr Ala Val Leu Leu Lys Phe Leu Gln
1               5                   10                  15

Ala Pro Tyr Gly Lys His Asn Arg Thr Gly Trp Gly Pro Thr Val Ser
            20                  25                  30

Pro Pro Ile Ala Trp Phe Val Met Glu Ser Pro Thr Leu Trp Leu Thr
        35                  40                  45

Leu Leu Leu Leu Pro Phe Gly Arg His Ala Leu Asn Pro Lys Ser Leu
    50                  55                  60

Leu Leu Phe Ser Pro Tyr Leu Ile His Tyr Phe Leu Arg Thr Ile Ile
65                  70                  75                  80

Tyr Pro Leu Arg Leu Phe Arg Ser Ser Phe Pro Ala Gly Lys Asn Gly
                85                  90                  95

Phe Pro Ile Thr Ile Ala Ala Leu Ala Phe Thr Phe Asn Leu Leu Asn
            100                 105                 110

Gly Tyr Ile Gln Ala Arg Trp Val Ser His Tyr Lys Asp Asp Tyr Glu
        115                 120                 125

Asp Gly Asn Trp Phe Trp Trp Arg Phe Val Ile Gly Met Val Val Phe
    130                 135                 140

Ile Thr Gly Met Tyr Ile Asn Ile Thr Ser Asp Arg Thr Leu Val Arg
145                 150                 155                 160

Leu Lys Lys Glu Asn Arg Gly Gly Tyr Val Ile Pro Arg Gly Gly Trp
                165                 170                 175

Phe Glu Leu Val Ser Arg Pro Asn Tyr Phe Gly Glu Ala Ile Glu Trp
            180                 185                 190

Leu Gly Trp Ala Val Met Thr Trp Ser Trp Ala Gly Ile Gly Phe Phe
        195                 200                 205

Leu Tyr Thr Cys Ser Asn Leu Phe Pro Arg Ala Arg Ala Ser His Lys
    210                 215                 220

Trp Tyr Ile Ala Lys Phe Lys Glu Glu Tyr Pro Lys Thr Arg Lys Ala
225                 230                 235                 240

Val Ile Pro Glu Val Tyr
                245
```

(2) INFORMATION FOR SEQ ID NO:4:

(i) SEQUENCE CHARACTERISTICS:
        (A) LENGTH: 239 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

```
Gly Phe Met Ala Phe Val Ser Ile Val Gly Leu Arg Ser Val Gly Ser
1               5                   10                  15

Pro Tyr Gly Arg Tyr Ser Pro Gln Trp Pro Gly Ile Arg Val Pro Ala
            20                  25                  30

Arg Pro Ala Trp Phe Ile Gln Glu Leu Pro Ser Met Ala Trp Pro Leu
        35                  40                  45

Tyr Glu Tyr Ile Arg Pro Ala Ala Ala Arg Leu Gly Asn Leu Pro Asn
    50                  55                  60

Arg Val Leu Leu Ala Met Phe Leu Ile His Tyr Val Gln Arg Thr Leu
65                  70                  75                  80
```

```
Val Phe Pro Val Leu Ile Arg Gly Gly Lys Pro Thr Leu Leu Val Thr
                85                  90                  95

Phe Val Leu Ala Phe Leu Phe Cys Thr Phe Asn Gly Tyr Val Gln Ser
            100                 105                 110

Arg Tyr Leu Ser Gln Phe Ala Val Tyr Ala Glu Asp Trp Val Thr His
            115                 120                 125

Pro Cys Phe Leu Thr Gly Phe Ala Leu Trp Leu Val Gly Met Val Ile
            130                 135                 140

Asn Ile His Ser Asp His Ile Leu Arg Asn Leu Arg Lys Pro Gly Glu
145                 150                 155                 160

Thr Gly Tyr Lys Ile Pro Arg Gly Gly Leu Phe Glu Tyr Val Ser Ala
                165                 170                 175

Ala Asn Tyr Phe Gly Glu Leu Val Glu Trp Cys Gly Phe Ala Leu Ala
            180                 185                 190

Ser Trp Ser Leu Gln Gly Val Val Phe Ala Leu Phe Thr Leu Ser Thr
            195                 200                 205

Leu Leu Thr Arg Ala Lys Gln His Gln Trp Tyr His Glu Lys Phe
210                 215                 220

Glu Asp Tyr Pro Lys Ser Arg Lys Ile Leu Ile Pro Phe Val Leu
225                 230                 235

(2) INFORMATION FOR SEQ ID NO:5:

(i) SEQUENCE CHARACTERISTICS:
        (A) LENGTH: 243 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

Ala Tyr Leu Gln Cys Ala Val Gly Cys Ala Val Phe Ala Arg Asn Arg
1               5                   10                  15

Gln Thr Asn Ser Val Tyr Gly Arg His Ala Leu Pro Ser His Arg Leu
            20                  25                  30

Arg Val Pro Ala Arg Ala Ala Trp Val Val Gln Glu Leu Pro Ser Leu
            35                  40                  45

Ala Leu Pro Leu Tyr Gln Tyr Ala Ser Glu Ser Ala Pro Arg Leu Arg
50                  55                  60

Ser Ala Pro Asn Cys Ile Leu Leu Ala Met Phe Leu Val His Tyr Gly
65                  70                  75                  80

His Arg Cys Leu Ile Tyr Pro Phe Leu Met Arg Gly Gly Lys Pro Met
                85                  90                  95

Pro Leu Leu Ala Cys Thr Met Ala Ile Met Phe Cys Thr Cys Asn Gly
            100                 105                 110

Tyr Leu Gln Ser Arg Tyr Leu Ser His Cys Ala Val Tyr Ala Asp Asp
            115                 120                 125

Trp Val Thr Asp Pro Arg Phe Leu Ile Gly Phe Gly Leu Trp Leu Thr
            130                 135                 140

Gly Met Leu Ile Asn Ile His Ser Asp His Ile Leu Arg Asn Leu Arg
145                 150                 155                 160

Lys Pro Gly Asp Thr Gly Tyr Lys Ile Pro Arg Gly Gly Leu Phe Glu
                165                 170                 175

Tyr Val Thr Ala Ala Asn Tyr Phe Gly Glu Ile Met Glu Trp Cys Gly
            180                 185                 190
```

```
Tyr Ala Leu Ala Ser Trp Ser Val Gln Gly Ala Ala Phe Ala Phe Phe
            195                 200                 205

Thr Phe Gly Phe Leu Ser Gly Arg Ala Lys Glu His His Glu Trp Tyr
            210                 215                 220

Leu Arg Lys Phe Glu Glu Tyr Pro Lys Phe Arg Lys Ile Ile Ile Pro
225                 230                 235                 240

Phe Leu Phe (2) INFORMATION FOR SEQ ID NO:6:

(i) SEQUENCE CHARACTERISTICS:
        (A) LENGTH: 238 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Leu Ala Thr Met Gly Thr Leu Ile Leu Cys Leu Gly Lys Pro Ala Ser
1               5                   10                  15

Tyr Gly Lys His Thr Glu Ser Val Ser Ser Gly Val Pro Phe Leu Pro
            20                  25                  30

Ala Arg Ile Ala Trp Phe Leu Gln Glu Leu Pro Ser Phe Val Val Ser
            35                  40                  45

Val Gly Met Leu Ala Trp Gln Pro Arg Ser Leu Phe Gly Pro Pro Gly
        50                  55                  60

Asn Val Leu Leu Ala Leu Phe Ser Ala His Tyr Phe His Arg Thr Phe
65                  70                  75                  80

Ile Tyr Ser Leu Leu Thr Arg Gly Arg Pro Phe Pro Ala Val Leu Phe
            85                  90                  95

Leu Arg Ala Thr Ala Phe Cys Ile Gly Asn Gly Leu Leu Gln Ala Tyr
            100                 105                 110

Tyr Leu Val Tyr Cys Ala Glu Tyr Pro Glu Glu Trp Tyr Thr Asp Val
            115                 120                 125

Arg Phe Ser Phe Gly Val Phe Leu Phe Ile Leu Gly Met Gly Ile Asn
            130                 135                 140

Ile His Ser Asp Tyr Thr Leu Arg Gln Leu Arg Lys Pro Gly Glu Val
145                 150                 155                 160

Ile Tyr Arg Ile Pro Arg Gly Gly Leu Phe Thr Tyr Val Ser Gly Ala
            165                 170                 175

Asn Phe Leu Gly Glu Ile Ile Glu Trp Ile Gly Tyr Ala Leu Ala Thr
            180                 185                 190

Trp Ser Val Pro Ala Phe Ala Phe Ala Phe Phe Thr Leu Cys Phe Leu
            195                 200                 205

Gly Met Gln Ala Phe Tyr His Arg Phe Tyr Leu Lys Met Phe Lys
            210                 215                 220

Asp Tyr Pro Lys Ser Arg Lys Ala Leu Ile Pro Phe Ile Phe
225                 230                 235

(2) INFORMATION FOR SEQ ID NO:7:

(i) SEQUENCE CHARACTERISTICS:
        (A) LENGTH: 241 amino acids
        (B) TYPE: amino acid
        (C) STRANDEDNESS: Not Relevant
        (D) TOPOLOGY: linear (ii) MOLECULE TYPE: protein
```

-continued (xi) SEQUENCE DESCRIPTION: SEQ ID NO:7:

```
Leu Val Ala Leu Gly Ala Leu Ala Leu Tyr Val Ala Lys Pro Ser Ser
 1               5                  10                  15

Ser Ser Gly Tyr Gly Lys His Thr Glu Ser Leu Lys Pro Ala Ala Thr
            20                  25                  30

Arg Leu Pro Ala Arg Ala Ala Trp Phe Leu Gln Glu Leu Pro Ser Phe
         35                  40                  45

Ala Val Pro Ala Gly Ile Leu Ala Arg Gln Pro Leu Ser Leu Phe Gly
     50                  55                  60

Pro Pro Gly Thr Val Leu Leu Gly Leu Phe Cys Val His Tyr Phe His
 65                  70                  75                  80

Arg Thr Phe Val Tyr Ser Leu Leu Asn Arg Gly Arg Pro Tyr Pro Ala
                 85                  90                  95

Ile Leu Ile Leu Arg Gly Thr Ala Phe Cys Thr Gly Asn Gly Val Leu
                100                 105                 110

Gln Gly Tyr Tyr Leu Ile Tyr Cys Ala Glu Tyr Pro Asp Gly Trp Tyr
            115                 120                 125

Thr Asp Ile Arg Phe Ser Leu Gly Val Phe Leu Phe Ile Leu Gly Met
    130                 135                 140

Gly Ile Asn Ile His Ser Asp Tyr Ile Leu Arg Gln Leu Arg Lys Pro
145                 150                 155                 160

Gly Glu Ile Ser Tyr Arg Ile Pro Gln Gly Gly Leu Phe Thr Tyr Val
                165                 170                 175

Ser Gly Ala Asn Phe Leu Gly Glu Ile Ile Glu Trp Ile Gly Tyr Ala
            180                 185                 190

Leu Ala Thr Trp Ser Leu Pro Ala Leu Ala Phe Ala Phe Phe Ser Leu
        195                 200                 205

Cys Phe Leu Gly Leu Arg Ala Phe His His His Arg Phe Tyr Leu Lys
    210                 215                 220

Met Phe Glu Asp Tyr Pro Lys Ser Arg Lys Ala Leu Ile Pro Phe Ile
225                 230                 235                 240

Phe
```